US007135481B2

(12) United States Patent
Brown

(10) Patent No.: US 7,135,481 B2
(45) Date of Patent: Nov. 14, 2006

(54) NAPHTHALIMIDE COMPOSITIONS AND USES THEREOF

(75) Inventor: Dennis M. Brown, Menlo Park, CA (US)

(73) Assignee: ChemGenex Pharmaceuticals, Inc., Menlo Park, CA (US)

( * ) Notice: Subject to any disclaimer, the term of this patent is extended or adjusted under 35 U.S.C. 154(b) by 0 days.

(21) Appl. No.: 11/067,074

(22) Filed: Feb. 25, 2005

(65) Prior Publication Data

US 2005/0142214 A1    Jun. 30, 2005

Related U.S. Application Data

(63) Continuation of application No. 10/273,801, filed on Oct. 17, 2002, now abandoned, which is a continuation-in-part of application No. 09/834,177, filed on Apr. 12, 2001, now Pat. No. 6,630,173.

(60) Provisional application No. 60/330,037, filed on Oct. 17, 2001, provisional application No. 60/197,103, filed on Apr. 12, 2000.

(51) Int. Cl.
*A61K 31/473* (2006.01)

(52) U.S. Cl. .................. 514/296; 514/274; 514/456; 514/533; 514/283

(58) Field of Classification Search ............... 424/649; 514/274, 456, 533, 283, 296
See application file for complete search history.

(56) References Cited

U.S. PATENT DOCUMENTS

| 5,420,137 | A  | 5/1995  | Brana et al. |
| 6,630,173 | B1 | 10/2003 | Brown |
| 6,734,178 | B1 | 5/2004  | Brown |
| 2002/0123469 | A1 | 9/2002 | Brown |
| 2003/0176496 | A1 | 9/2003 | Medford et al. |
| 2004/0047918 | A1 | 3/2004 | Brown |
| 2004/0077629 | A1 | 4/2004 | Brown |
| 2004/0082565 | A1 | 4/2004 | Brown |
| 2004/0082788 | A1 | 4/2004 | Brown |
| 2004/0185117 | A1 | 9/2004 | Brown |
| 2005/0170015 | A1 | 8/2005 | Brown |
| 2005/0192312 | A1 | 9/2005 | Brown |

FOREIGN PATENT DOCUMENTS

| FR | 2 673 944 A1 | 9/1992 |
| WO | WO 01/68098 A2 | 9/2001 |

OTHER PUBLICATIONS

Malonne et al., Anti-Cancer Drugs, 8/9 (811-822) (1997) (abstract).*
Scheithauer et al., Breast Cancer Research and Treatment, 20:63-67 (1991).*
Twentyman, P.R. et al., Journal of the National Cancer Institute, 64(3), (Mar. 1980), 595-604.*

Abbott, B.J., et al., "Screening Data from the Cancer Chemotherapy National Service Center Screening Laboratories. XXXVI. Plant Extracts," *Cancer Res. Supp.*, 26(9):1131-1136 (Sep. 1966).
Ajani, J.A., et al., "*In vitro* activity of amonafide against primary human tumors compared with the activity of standard agents," *Invest. New Drugs*, 6(2):79-85 (Jun. 1988).
Asbury, R.F., et al., "A Gynecological Oncology Group phase II study of amonafide (NSC #308847) in sqamous cell carcinoma of the cervix," *Am. J. Clin. Oncol.*, 17(2):125-128 (Apr. 1994).
Bernges, F., et al., "Combination effects of poly(ADP-ribose) polymerase inhibitors and DNA-damaging agents in ovarian tumor cell lines—with special reference to cisplatin," *J. Cancer Res. Clin. Oncol.*, 122(11):665-670 (1996).
Cobb, P.W., et al., "Activity of DMP 840, a new bis-naphthalimide, on primary human tumor colony-forming units," *J. Natl Cancer Inst.*, 86(19):1462-1465 (Oct. 1994).
Costanza, M.E., et al., "Amonafide: An Active Agent in the Treatment of Previously Untreated Advanced Breast Cancer—A Cancer and Leukemia Group B Study (CALGB 8642)," *Clin. Cancer Res.* 1(7):699-704 (Jul. 1995).
Costanza, M.E., et al., "Safety and efficacy of using a single agent or a phase II agent before instituting standard combination chemotherapy in previously untreated metastatic breast cancer patients: report of a randomized study—Cancer and Leukemia Group B 8642," *J. Clin. Oncol.*, 17(5):1397-1406 (May 1999).
Evans, W.K., et al., "Phase II study of amonafide: results of treatment and lessons learned from the study of an investigational agent in previously untreated patients with extensive small-cell lung cancer," *J. Clin. Oncol.*, 8(3):390-395 (Mar. 1990).
Gallion, H.H., et al., "Phase II trial of amonafide in previously treated patients with advanced ovarian cancer: a Southwest Oncology Group study," *Gynecol. Oncol.*, 46(2);230-232 (Aug. 1992).
Günther, A., et al., "Differential Expression of Intermediate-Filament Proteins in Murine Sarcoma 180 Ascites or Solid Tumor," *Cancer Res.*, 44(6):2590-2594 (Jun. 1984).
Hayes, D.F., et al., "Treatment of metastatic breast cancer: present and future prospects," *Semin. Oncol.*, 22(2 Supp. 5):5-19; disc. 19-21 (Apr. 1995).
Innocenti, F., "Pharmacogenetics: a tool for individualizing antineoplastic therapy," *Clin. Pharmacokinet.*, 39(5):315-325 (Nov. 2000).
Jin, X., et al., "Cisplatin combination therapy of murine S180," *Shanghai Yike Daxue Xeubao*, 16(1):50-54 (1989), Caplus Accession No. 1989:225174, (Abstract Only).
Laster, W.R., et al., "Therapeutic synergism (TS) of homoharringtonine (H) plus 5-fluorouracil (FU) against leukemia P388 (P388/0) and ARA-C-resistant P388 (P388/ARA-C)," *Proc. Am. Assn. Cancer Res.*, 23:786 (1982), Embase Accession No. 82182588, (Abstract only).

(Continued)

*Primary Examiner*—Phyllis G. Spivack
(74) *Attorney, Agent, or Firm*—Dorsey & Whitney LLP; Richard F. Trecartin

(57) ABSTRACT

Methods of treating a solid tumor are disclosed comprising administering amonafide in combination with an antiproliferative agent.

13 Claims, 3 Drawing Sheets

OTHER PUBLICATIONS

Magnusson, K., et al., "Is conversion of solid into more anoxic ascites tumors associated with p53 inactivation?," *Oncogene*, 17(5):2333-2337 (Nov. 1998).

Malonne, H., et al., "DNA topoisomerase targeting drugs: Mechanisms of action and perspectives," *Anti-Cancer Drugs*, 8(9):811-822 (1997) (Abstract only).

Pérez, J.M., et al., "Combined effect of platination and intercalation upon DNA binding of novel cytotoxic Pt-bis(naphthalimide) complexes," *J. Med. Chem.*, 42(26):5482-5486 (Dec. 1999).

Powell, R.G., "Antitumor alkaloids for *Cephalotaxus harringtonia*: structure and activity," *J. Pharm. Sci.* 61(8):1227-1230 (Aug. 1972).

Provencher, D., et al., "Discordance in p53 Mutations When Comparing Ascites and Solid Tumors from Patients with Serious Ovarian Cancer," *Tumor Biol.*, 18(3):167-174 (1997).

Savage, K.E., et al., "Effect of tunicamycin, an inhibitor of protein glycosylation, on division of tumor cells *in vitro*," 64:295-306 (Nov. 1983).

Takano, I., et al., "Ester-type *Cephalotaxus* alkaloids from *Cephalotaxus harringtonia* var. *drupacea*," *Phytochemistry*, 44(4):735-738 (1997).

Takano, I., et al., "Ester-type *Cephalotaxus* alkaloids from *Cephalotaxus harringtonia* var. *drupacea*," *Phytochemistry*, 44(4):735-738 (1997).

Visani, G., et al., "Effects of homoharringtonine alone and in combination with alpha interferon and cytosine arabinoside on *in vitro* growth and induction of apoptosis in chronic myeloid leukemia and normal hematopoietic progenitors," *Leukemia*, 11:624-628 (May 1997).

Wong, K., et al., "Management of metastatic breast cancer," *World J. Surg.*, 18(1):98-111 (Jan.-Feb. 1994).

Yuzhu, Z., et al., "Homoharringtonine, cytarabine and aclarubicin (HAA) combination chemotherapy for acute myeloid leukemia (AML)," *Chin. J. Clin. Oncol.*, 25(10):758-759 (1998), Embase Accession No. 1998384948, (Abstract only).

Zhang, S.D., et al., "Inhibitory effects of homoharringtonine and hydroxycamptothecin in combination with other agents on cancer cell growth," *Asia Pac. J. Pharmacol.*, 7:191-195 (1992).

\* cited by examiner

Amonafide:
$R_1 = NH_2$
$R_2 =$

NAPHTHALIMIDE COMPOSITIONS AND USES THEREOF

This application is a continuation of U.S. Ser. No. 10/273,801, filed Oct. 17, 2002, now abandoned and claims the benefit of U.S. Provisional Application Number 60/330,037, filed Oct. 17, 2001, which is a continuation-in-part application of U.S. Ser. No. 09/834,177, filed Apr. 12, 2001, now U.S. Pat. No. 6,630,173 which claims the benefit of U.S. Provisional Application No. 60/197,103, filed Apr. 12, 2000.

FIELD OF THE INVENTION

The technical field of the invention is the use of naphthalimides with antiproliferative agents to treat a host with a cellular proliferative disease.

BACKGROUND OF THE INVENTION

There is considerable interest in modulating the efficacy of currently used antiproliferative agents to increase the rates and duration of antitumor effects associated with conventional antineoplastic agents.

Conventional antiproliferative agents used in the treatment of cancer are broadly grouped as (1) chemical compounds which affect the integrity of nucleic acid polymers by binding, alkylating, inducing strand breaks, intercalating between base pairs or affecting enzymes which maintain the integrity and function of DNA and RNA; (2) chemical agents that bind to proteins to inhibit enzymatic action (e.g., antimetabolites) or the function of structural proteins necessary for cellular integrity (e.g., antitubulin agents). Other, chemical compounds that have been identified to be useful in the treatment of some cancers include drugs which block steroid hormone action for the treatment of breast and prostate cancer, photochemically activated agents, radiation sensitizers, and protectors.

Of special interest to this invention are those compounds that directly affect the integrity of the genetic structure of the cancer cells. Nucleic acid polymers such as DNA and RNA are prime targets for anticancer drugs. Alkylating agents such as nitrogen mustards, nitrosoureas, aziridine containing compounds directly attack DNA. Metal coordination compounds such as cisplatin and carboplatin similarly directly attack the nucleic acid structure resulting in lesions that are difficult for the cells to repair which, in turn, can result in cell death. Other nucleic acid affecting compounds include anthracycline molecules such as doxorubicin, which intercalates between the nucleic acid base pairs of DNA polymers, bleomycin, which causes nucleic acid strand breaks, fraudulent nucleosides such as pyrimidine and purine nucleoside analogs, which are inappropriately incorporated into nucleic polymer structures and ultimately cause premature DNA chain termination. Certain enzymes that affect the integrity and functionality of the genome can also be inhibited in cancer cells by specific chemical agents and result in cancer cell death. These include enzymes that affect ribonucleotide reductase (e.g., hydroxyurea, gemcitabine), topoisomerase I (e.g., camptothecin) and topoisomerase II (e.g., etoposide).

One of the most broadly used of these DNA targeted anticancer drugs is cisplatin (cis-diamminedichloroplatinum II, CDDP). This compound is active against several human cancers including testicular, small-cell lung, bladder, cervical and head and neck cancer.

Although the clinical activity of currently approved antiproliferative agents against many forms of cancers can be shown, improvements in tumor response rates, duration of response and ultimately patient survival are still sought. The invention described herein demonstrates the novel use of the naphthalimides and analogs thereof, including amonafide, which can potentiate the antitumor effects of chemotherapeutic drugs, in particular, agents affecting the integrity of nucleic polymers such as DNA.

SUMMARY OF THE INVENTION

Methods and compositions are provided for the treatment of a host having a cellular proliferative disease, particularly a neoplasia. In the subject methods, pharmaceutically acceptable naphthalimide and an antiproliferative agent are administered in an amount sufficient to modulate the cellular proliferative disease.

DETAILED DESCRIPTION OF THE FIGURES

DETAILED DESCRIPTION OF THE INVENTION

Figure 1:
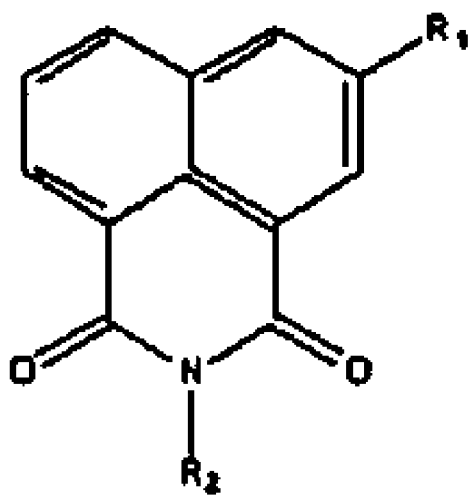
FIG. 1 depicts the general structure of a naphthalimide analog. $R_1$ and $R_2$ represent substitution groups. The structures of $R_1$ and $R_2$ for the naphthalimide analog, amonafide, are shown.
Figure 1:
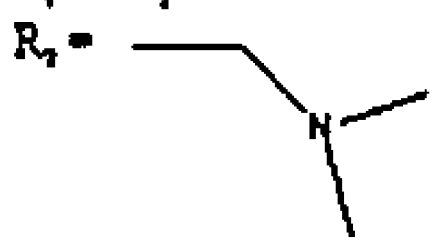

Methods and compositions are provided for the treatment of a host with a cellular proliferative disease, particularly a neoplasia. In the subject methods, a pharmaceutically acceptable naphthalimide is administered, preferably systemically, in conjunction with an antiproliferative agent to improve the anticancer effects. In a preferred embodiment, the naphthalimide provides a chemopotentiator effect.

Methods and compositions are provided herein for the treatment of a host. A "host" for the purposes of the present invention includes both humans and other animals, particularly mammals, and organisms. Thus the methods are applicable to both human therapy and veterinary applications. In the preferred embodiment the patient is a mammal, and in the most preferred embodiment the patient is human.

The methods of the invention are used to treat a cellular proliferative disease. According to a preferred embodiment, the cellular proliferative disease is a tumor, e.g., a solid tumor. Solid tumors that are particularly amenable to treatment by the claimed methods include carcinomas and sarcomas. Carcinomas include those malignant neoplasms derived from epithelial cells which tend to infiltrate (invade) the surrounding tissues and give rise to metastases. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue.

It will be understood that the method of the invention is not limited to the treatment of these tumor types, but extends to any solid tumor derived from any organ system.

Cellular proliferative diseases that can be treated by the methods and compositions of the invention include, for example, psoriasis, skin cancer, viral induced hyperproliferative HPV-papiloma, HSV-shingles, colon cancer, bladder cancer, breast cancer, melanoma, ovarian carcinoma, prostatic carcinoma, or lung cancer, and a variety of other cancers as well.

The agents are provided in amounts sufficient to modulate a cellular proliferative disease. In one embodiment, modulation of a cellular proliferative disease comprises a reduction in tumor growth. In another embodiment, modulation of a disease comprises inhibition of tumor growth. In another embodiment, modulation of a cellular proliferative disease comprises an increase in tumor volume quadrupling time (described below). In another embodiment, modulation of a cellular proliferative disease comprises a chemopotentiator effect. In another embodiment, modulation of a disease comprises a chemosensitizing effect. In other embodiments, modulation of a disease comprises cytostasis. In still other embodiments, modulation of a disease comprises a cytotoxic effect.

The agents are administered to a host by a variety of routes. According to one embodiment, a naphthalimide is administered by injection, preferably by parenteral, e.g., intravenous, injection. According to one embodiment, an antiproliferative agent is administered by injection, preferably by intravenous injection. The mode of administration of the agents may be the same or different for each. Thus, the compounds may be administered in a single dosage form, one may be administered orally and the other intravenously, one may be administered continuously and the other intermittently, etc.

Any suitable route of administration may be employed for providing a mammal, especially a human, with an effective dosage of the compounds of the invention. For example, oral, rectal, topical, parenteral, ocular, pulmonary, nasal, etc. routes may be employed. Dosage forms include tablets, troches, dispersions, suspensions, solutions, capsules, creams, ointments, aerosols, and the like. The routes of administration may be the same or different for each of the two compounds.

Disclosed herein are methods of treatment comprising contacting a host with a naphthalimide in conjunction with an antiproliferative agent. By "in conjunction with" is meant that the two agents are administered such that both agents are present and active in the host together during at least a portion of the treatment schedule. According to one embodiment, the two agents are administered simultaneously, in a single dosage form.

According to an alternative embodiment, the administration of one agent is followed by administration of the other agent. For example, administration of a naphthalimide may be followed by administration of an antiproliferative agent; or administration of an antiproliferative agent may be followed by administration of a naphthalimide.

When administration of the two agents is not simultaneous, a defined length of time may separate the two agents. According to one embodiment, administration of each agent is separated by at least about 5 minutes but by no more than 4 hours. Generally, when administration of the two agents is not simultaneous, the time separating the administration of each agent is no more than two plasma half lives of the first administered agent. According to a preferred embodiment, administration of each agent is separated by about 30 minutes. According to another embodiment, administration of each agent is separated by about 1 hour. According to another embodiment, administration of each agent is separated by about 2 hours.

The optimal time separating the administration of the agents will vary depending on the dosage used, the clearance rate of each agent, and the particular host treated. According to the claimed methods, the naphthalimide and the antiproliferative agent used are administered such that the agents are both present together in the host system in active form during the treatment of the host. That is, the agent that is administered first will be present in the host in an active form after the second agent is administered.

A chemical agent is a "chemopotentiator" when it enhances the effect of a known antiproliferative drug in a more than additive fashion relative to the activity of the chemopotentiator or antiproliferative agent used alone. In some cases, a "chemosensitizing" effect may be observed. This is defined as the effect of use of an agent that if used alone would not demonstrate significant antitumor effects but would improve the antitumor effects of an antiproliferative agent in a more than additive fashion than the use of the antiproliferative agent by itself.

As used herein, the term "naphthalimide" includes all members of that chemical family including benzisoquinolinedione and analogs thereof. The naphthalimide family is defined by chemical structure as depicted in FIG. 1.

A naphthalimide analog is further defined but not limited to substituent changes in $R_1$ and $R_2$ (FIG. 1). Examples of $R_1$ and $R_2$ include those listed in Table 1. In a preferred embodiment, a naphthalimide analog has the structure of amonafide, shown in FIG. 2.

TABLE 1

| Group | Substitution | Length |
|---|---|---|
| $R_1$ | Alkyl | $C_1 \rightarrow C_5$ |
|  | Amino |  |
|  | Nitro |  |
|  | Cyano |  |
|  | Alkoxy | $OC_1 \rightarrow OC_5$ |
|  | Hydrogen |  |
| $R_2$ | Alkyl | $C_1 \rightarrow C_5$ |

"Alkyl" means a straight-chain or branched-chain alkyl radical containing from 1 to 10, preferably from 1 to 6, and more preferably from 1 to 4, carbon atoms. Examples of such radicals include methyl, ethyl, n-propyl, isopropyl, n-butyl, isobutyl, sec-butyl, tert-butyl, pentyl, iso-amyl, hexyl, and decyl. "Alkoxy" means an alkyl ether radical. Examples of alkyl ether radicals include methoxy, ethoxy, n-propoxy, iso-propoxy, n-butoxy, iso-butoxy, sec-butoxy, and tert-butoxy.

Figure 2:
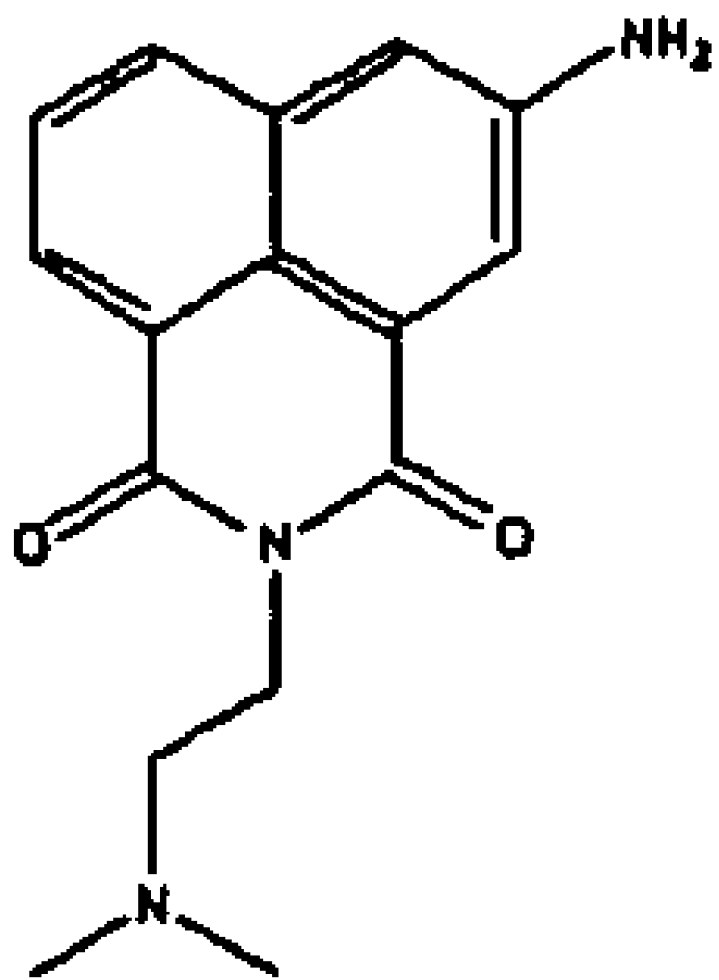
FIG. 2 depicts the structure of the naphthalimide analog, amonafide.
Figure 3:
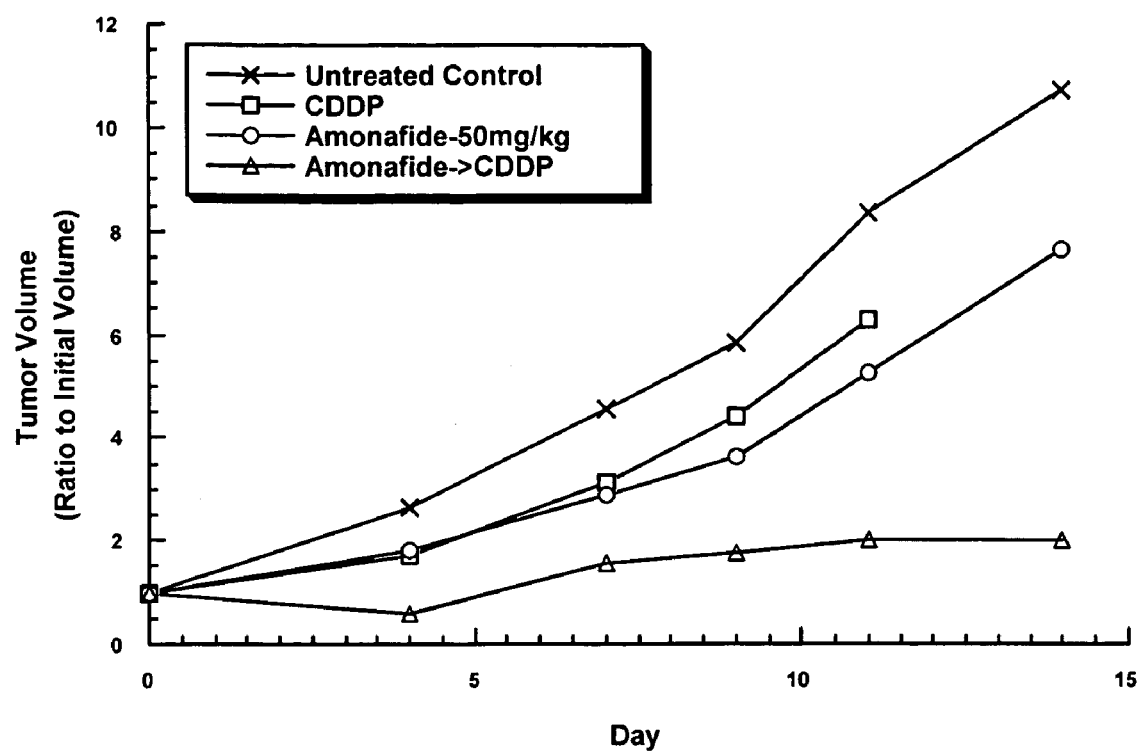
FIG. 3 shows tumor growth delay, as tumor volume on days after treatment with the naphthalimide analog, amonafide, amonafide followed by CDDP, or CDDP alone.

A naphthalimide analog is a further chemical refinement. A specific example of a naphthalimide analog is amonafide which is also known by the following chemical synonyms: Nafidamide; Benzisoquinolinedione; 5-amino-2-[(dimethylamine)ethyl]-1H-benz[de-]isoquinoline-1,3-(2H)-dione (FIG. 2).

As used herein, antiproliferative agents are compounds which induce cytostasis or cytotoxicity. "Cytostasis" is the inhibition of cells from growing while "cytotoxicity" is defined as the killing of cells.

Specific examples of antiproliferative agents include: antimetabolites, such as methotrexate, 5-fluorouracil, gemcitabine, cytarabine, pentostatin, 6-mercaptopurine, 6-thioguanine, L-asparaginase, hydroxyurea, N-phosphonoacetyl-L-aspartate (PALA), fludarabine, 2-chlorodeoxyadenosine, and floxuridine; structural protein agents, such as the vinca alkaloids, including vinblastine, vincristine, vindesine, vinorelbine, paclitaxel, and colchicine; agents that affect NF-κB, such as curcumin and parthenolide; agents that affect protein synthesis, such as homoharringtonine; antibiotics, such as dactinomycin, daunorubicin, doxorubicin, idarubicin, bleomycins, plicamycin, and mitomycin; hormone antagonists, such as tamoxifen and luteinizing hormone releasing hormone (LHRH) analogs; nucleic acid damaging agents such as the alkylating agents mechlorethamine, cyclophosphamide, ifosfamide, chlorambucil, dacarbazine, methylnitrosourea, semustine (methyl-CCNU), chlorozotocin, busulfan, procarbazine, melphalan, carmustine (BCNU), lomustine (CCNU), and thiotepa, the intercalating agents doxorubicin, dactinomycin, daurorubicin and mitoxantrone, the topoisomerase inhibitors etoposide, camptothecin and teniposide, and the metal coordination complexes cisplatin and carboplatin.

Also claimed herein are pharmaceutical compositions comprising a naphthalimide and an antiproliferative agent. The naphthalimide and antiproliferative agent may be in intimate admixture or they may isolated from each other. According to one embodiment, the claimed pharmaceutical compositions comprise pharmaceutically acceptable salts of a naphthalimide or antiproliferative agent. According to one embodiment, the claimed pharmaceutical compositions may contain pharmaceutically acceptable carriers and, optionally, other therapeutically active ingredients.

The agents may be provided in a range of concentrations, depending on the cellular proliferative disease to be treated, host species, clearance rate of each agent, drug absorption, bioavailability, mode of administration. In a preferred embodiment, a naphthalimide is provided for administration at between about 1–30 mg/kg or 50–1000 mg/m$^2$ In a preferred embodiment, an antiproliferative agent is provided for administration at between about 0.1–50 mg/kg. Generally the concentration administered will depend on a variety of factors, including the dose and schedule that are optimal for the antiproliferative agent used, as known and understood by those of skill in the art.

The compositions include compositions suitable for oral, rectal, topical (including transdermal devices, aerosols, creams, ointments, lotions, and dusting powders), parenteral (including subcutaneous, intramuscular, and intravenous), ocular (ophthalmic), pulmonary (nasal or buccal inhalation), or nasal administration; although the most suitable route in any given case will depend largely on the nature and severity of the condition being treated and on the nature of the active ingredient. The agents may be conveniently presented in unit dosage form and prepared by any of the methods well known in the art of pharmacy.

For example, compounds of the invention may be administered orally, for example in tablet form, or by inhalation, for example in aerosol or other atomisable formulations or in dry powder formulations, using an appropriate inhalation device such as those known in the art. The compounds of the invention may also be administered intranasally.

In the case of oral delivery, the dosage form would allow that suitable concentrations of a naphthalimide would be provided in a form such that an adequate plasma level could be achieved to provide the chemopotentiation of the other chemotherapeutic compound(s). Tablets, capsules, suspensions or solutions may contain 10 milligrams to 2 grams per dose treatment to achieve the appropriate plasma concentrations.

A compound of the invention may be combined as the active ingredient in intimate admixture with a pharmaceutical carrier according to conventional pharmaceutical compounding techniques. The carrier may take a wide variety of forms depending on the nature of the preparation desired for administration, i.e., oral, parenteral, etc. In preparing oral dosage forms, any of the usual pharmaceutical media may be used, such as water, glycols, oils, alcohols, flavoring agents, preservatives, coloring agents, and the like in the case of oral liquid preparations (e.g., suspensions, elixirs, and solutions); or carriers such as starches, sugars, microcrystalline cellulose, diluents, granulating agents, lubricants, binders, disintegrating agents, etc. in the case of oral solid preparations such as powders, capsules, and tablets. Solid oral preparations are preferred over liquid oral preparations. Because of their ease of administration, tablets and capsules are the preferred oral dosage unit form. If desired, capsules may be coated by standard aqueous or non-aqueous techniques.

In addition to the dosage forms described above, the compounds of the invention may be administered by controlled release means and devices.

Pharmaceutical compositions of the present invention suitable for oral administration may be prepared as discrete units such as capsules, cachets, or tablets each containing a predetermined amount of the active ingredient in powder or granular form or as a solution or suspension in an aqueous or nonaqueous liquid or in an oil-in-water or water-in-oil emulsion. Such compositions may be prepared by any of the methods known in the art of pharmacy. In general, the compositions are prepared by uniformly and intimately admixing the active ingredient with liquid carriers, finely divided solid carriers, or both and then, if necessary, shaping the product into the desired form. For example, a tablet may be prepared by compression or molding, optionally with one or more accessory ingredients. Compressed tablets may be prepared by compressing in a suitable machine the active ingredient in a free-flowing form such as powder or granule optionally mixed with a binder, lubricant, inert diluent, or surface active or dispersing agent. Molded tablets may be made by molding in a suitable machine, a mixture of the powdered compound moistened with an inert liquid diluent.

Ophthalmic inserts are made from compression molded films which are prepared on a Carver Press by subjecting the powdered mixture of active ingredient and HPC to a compression force of 12,000 lb. (gauge) at 149.degree. C. for 1–4 min. The film is cooled under pressure by having cold water circulate in the platen. The inserts are then individually cut from the film with a rod-shaped punch. Each insert is placed in a vial, which is then placed in a humidity cabinet (88% relative humidity at 30.degree. C.) for 2–4 days. After removal from the cabinet, the vials are capped and then autoclaved at 121.degree. C. for 0.5 hr.

The inhalable form may be, for example, an atomisable composition such as an aerosol comprising the compounds of the invention in solution or dispersion in a propellant or a nebulizable composition comprising a dispersion of the compound of the invention in an aqueous, organic or aqueous/organic medium, or a finely divided particulate form comprising the compounds of the invention in finely divided form optionally together with a pharmaceutically acceptable carrier in finely divided form.

The compositions containing a compound of this invention may also comprise an additional agent selected from the group consisting of cortiocosteroids, bronchodilators, anti-asthmatics (mast cell stabilizers), anti-inflammatories, antirheumatics, immunosuppressants, antimetabolites, immunomodulators, antipsoriatics, and antidiabetics. Specific compounds include theophylline, sulfasalazine and aminosalicylates (anti-inflammatories); cyclosporin, FK-506, and rapamycin (immunosuppressants); cyclophosphamide and methotrexate (antimetabolites); and interferons (immunomodulators).

An aerosol composition suitable for use as the inhalable form may comprise the compounds of the invention in solution or dispersion in a propellant, which may be chosen from any of the propellants known in the art. Suitable such propellants include hydrocarbons such as n-propane, n-butane or isobutane or mixtures of two or more such hydrocarbons, and halogen-substituted hydrocarbons, for example fluorine-substituted methanes, ethanes, propanes, butanes, cyclopropanes or cyclobutanes, particularly 1,1,1,2-tetrafluoroethane (HFA134a) and heptafluoropropane (HFA227), or mixtures of two or more such halogen-substituted hydrocarbons. Where the compounds of the invention are present in dispersion in the propellant, i.e. where present in particulate form dispersed in the propellant, the aerosol composition may also contain a lubricant and a surfactant, which may be chosen from those lubricants and surfactants known in the art. The aerosol composition may contain up to about 5% by weight, for example 0.002 to 5%, 0.01 to 3%, 0.015 to 2%, 0.1 to 2%, 0.5 to 2% or 0.5 to 1%, by weight of the compounds of the invention, based on the weight of the propellant. Where present, the lubricant and surfactant may be in an amount up to 5% and 0.5% respectively by weight of the aerosol composition. The aerosol composition may also contain ethanol as co-solvent in an amount up to 30% by weight of the composition, particularly for administration from a pressurized metered dose inhalation device.

A finely divided particulate form, i.e. a dry powder, suitable for use as the inhalable form may comprise the compounds of the invention in finely divided particulate form, optionally together with a finely divided particulate carrier, which may be chosen from materials known as carriers in dry powder inhalation compositions, for example saccharides, including monosaccharides, disaccharides and polysaccharides such as arabinose, glucose, fructose, ribose, mannose, sucrose, lactose, maltose, starches or dextran. As especially preferred carrier is lactose. The dry powder may be in capsules of gelatin or plastic, or in blisters, for use in a dry powder inhalation device, preferably in dosage units of 5 .mu.g to 40 mg of the active ingredient. Alternatively, the dry powder may be contained as a reservoir in a multi-dose dry powder inhalation device.

In the finely divided particulate form, and in the aerosol composition where the compounds of the invention are present in particulate form, the compound of the invention may have an average particle diameter of up to about 10 .mu.m, for example 1 to 5 .mu.m. The particle size of the compound of the invention, and that of a solid carrier where present in dry powder compositions, can be reduced to the desired level by conventional methods, for example by grinding in an air-jet mill, ball mill or vibrator mill, micro-precipitation, spray-drying, lyophilisation or recrystallisation from supercritical media.

The inhalable medicament comprising the pharmaceutical compositions of the invention may be administered using an inhalation device suitable for the inhalable form, such devices being well known in the art. Accordingly, the invention also provides a pharmaceutical product comprising the compounds of the invention in inhalable form as hereinbefore described in association with an inhalation device. In a further aspect, the invention provides an inhalation device containing the compounds of the invention in inhalable form as hereinbefore described.

Where the inhalable form is an aerosol composition, the inhalation device may be an aerosol vial provided with a valve adapted to deliver a metered dose, such as 10 to 100 .:l, e.g. 25 to 50 .:l, of the composition, i.e. a device known as a metered dose inhaler. Suitable such aerosol vials and procedures for containing within them aerosol compositions under pressure are well known to those skilled in the art of inhalation therapy. Where the inhalable form is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 mL, commonly 1 to 10 mL, of the dispersion; or a hand-held nebulizer such as an AERX (ex Aradigm, US) or BINEB (Boehringer Ingelheim) nebulizer which allows much smaller nebulized volumes, e.g. 10 to 100 .mu.l, than conventional nebulizers. Where the inhalable form is the finely divided particulate form, the inhalation device may be, for example, a dry powder inhalation device adapted to deliver dry powder from a capsule or blister containing a dosage unit of the dry powder or a multidose dry powder inhalation device adapted to deliver, for example, 25 mg of dry powder per actuation. Suitable such dry powder inhalation devices are well known.

The pharmaceutical compostions of the invention may be synthesized using known techniques. According to one embodiment, the naphthalimides used in the present invention is amonafide synthesized according to a method disclosed in U.S. provisional application Ser. No. 60/394,558, filed Jul. 8, 2002, hereby incorporated by reference in its entirety.

The following examples are offered by way of illustration and not by way of limitation.

EXAMPLE 1

Chemopotentiation of Cisplatin by Amonafide

Transplantable experimental murine fibrosarcomas (2×105 RIF-1 cells) were grown intradermally in the flanks of 3 month old female C3H mice (Charles River, Holister, Calif.). When the tumors reached a volume of approximately 100 mm3, the mice were randomly assigned to each experimental group (4 mice per group).

The experimental compositions were prepared as described in Table 2.

TABLE 2

| Agent | Dose | Solvent | Supplier |
|---|---|---|---|
| Amonafide | 50 mg/kg | DMSO | NCI |
| Cisplatin | 4 mg/kg | Water for injection | David Bull Labs |

The chemopotentiator, amonafide, was obtained from NCI and was made to the appropriate concentration in DMSO. Cisplatin (David Bull Laboratories- Mulgrave, Australia, lot. 5201844x) was made to the appropriate concentration in water for injection. The compositions were injected systemically (i.e., intraperitoneally, i.p.), in a volume of 100 microliters. For the treatment of group 3, the chemopotentiator, amonafide, was injected 30 minutes prior to the injection of cisplatin. After treatment, the growth of the tumors was monitored three times per week by caliper measurements of three perpendicular diameters of the tumor and calculation of tumor volume from the formula:

$$V = \pi/6 \times D_1 \times D_2 \times D_3,$$

where $D_{1-3}$ represents tumor diameters, in mm.

The tumors were followed until they reached a size of four times their day zero treatment volume (TVQT), or up to 30 days after treatment, whichever came first. The data is expressed as the "tumor volume quadrupling time" (TVQT) mean and as the "delay." Mean TVQT is the mean days required for individual tumors to grow to four times the tumor volume at the initial treatment day. The "delay" is the median of days required for a tumor to grow to four times the mean size of the treated group, minus the median of days required to grow to four times the mean size of the control group. The data is also expressed as the ratio of the tumor volume quadrupling time of the treated tumor over the untreated control group (TVQT/CTVQT). Increasing values of this ratio indicate increased antitumor response.

The data is presented in Table 3 below and in FIG. 2.

TABLE 3

| Group | Treatment | Dose (mg/kg) | Mean TVQT ± S.E. | TVQT/CTVQT | Median (TVQT) | Delay (Days) |
|---|---|---|---|---|---|---|
| 1 | Untreated Control | — | 6.3 ± 0.3 | 1.0 | 6 | 0.00 |
| 2 | Amonafide | 50 | 9.7 ± 0.6 | 1.5 | 9.0 | 2.94 |
| 3 | Amonafide → Cisplatin | 50 → 4 | 17.9 | 2.8 | 17.9 | 11.81 |
| 4 | Cisplatin | 4 | 8.4 ± 0.3 | 1.3 | 8.1 | 2.10 |

The arrow → in Group 3 indicates administration 30 minutes following administration of amonafide.

The results of Table 3 indicate that the antiproliferative activity of cisplatin is enhanced by the use of the chemopotentiator, amonafide in that a more than additive effect was observed when both compounds were used to treat the tumor bearing mice (group 3) in comparison to the use of cisplatin alone (group 4) or amonafide alone (group 2).

EXAMPLE 2

Effect of Amonafide, Alone and in Combination with Other Chemotherapeutics on RIF-1 Tumor Growth in C3H Mice The RIF-1 murine fibrosarcoma tumor model was used to evaluate the antitumor activity of amonafide, alone and in combination with various antiproliferative agents. The antiproliferative agents used include those that affect nucleic acid (e.g., DNA) integrity (e.g., cisplatin, etoposide, 5-fluorouracil), agents that affect structural or cytoplasmic proteins or their synthesis (e.g., homoharringtonine, paclitaxel, vinblastine, colchicine, curcumin or parthenolide).

Amonafide-NCI was obtained from NCI as a powder. Amonafide-Penta was obtained from Penta Biotech (Union City, Calif.), Lot No.039-01, as a powder. Cisplatin for Injection, USP, was obtained from David Bull Labs (Mulgrave, Australia), Lot No. 5201844x, as a lypholized powder. Paclitaxel was obtained from Bristol Myers Squibb Co. (Princeton, N.J.), Lot No. 9J16241, exp. Sep. 2001, prediluted to 6 mg/mL in Cremaphor/EL. Vinblastine was obtained from Bedford Labs (Bedford, Ohio), Lot No. 112647, as a lypholized powder. Etoposide was obtained from Pharmacia (Kalamazoo, Mich.), Lot No. ETA013, exp. May 1999, as a liquid prediluted to 20 mg/mL. 5-Fluorouracil was obtained from Pharmacia (Kalamazoo, Mich.), Lot No. FFA191, exp. Jul. 2000, liquid prediluted to 50 mg/mL. Curcumin was obtained from Sigma (St. Louis, Mo.), Lot No. 69H3457. Parthenolide was obtained from Tocris (Ballwin, Mo.) Lot No. 7/18089. DMSO was obtained from Sigma (St. Louis, Mo.), Lot No. 80K3695. 0.9% Sodium Chloride for Injection, USP (saline) was manufactured by Abbott Laboratories (Lot No. 55-199-DK). Sterile Water for Injection, USP (WFI) was manufactured by Lyphomed, Inc. (Lot No. 390849).

Formulations: Test preparations (treatment groups) are summarized in Table 4.

TABLE 4

Summary of Treatment Groups

| Formulation | Treatment | Concentration (mg/mL) | Route of Administration | Injection Volume (µL) |
|---|---|---|---|---|
| 1 | Amonafide-NCI in DMSO | 12.5 | IP | 100 |
| 2 | Amonafide-Penta in DMSO | 12.5 | IP | 100 |
| 3 | Amonafide-Penta in Saline | 7.5 | IP | 100 |
| 4 | CDDP in WFI | 1 | IP | 100 |
| 5 | Paclitaxel in WFI | 2.5 | IP | 100 |
| 6 | Vinblastine in saline | 0.5 | IP | 100 |
| 7 | Etoposide in saline | 2.5 | IP | 100 |
| 8 | 5-Fluorouracil in saline | 3.75 | IP | 100 |
| 9 | 5-Fluorouracil in saline | 7.5 | IP | 100 |
| 10 | Colchicine in saline | 2.5 | PO | 100 |
| 11 | HHT-Clin in WFI | 1 | IP | 100 |
| 12 | Curcumin in DMSO | 6.25 | IP | 100 |
| 13 | Parthenolide in DMSO | 5 | IP | 100 |

For preparation of formulation 1 and 2, amonafide was weighed into vials and dissolved in DMSO at 12.5 mg/mL.

For formulation 3, amonafide was weighed into vials and dissolved in saline.

For formulation 4, the contents of a 10-mg vial of lyophilized CDDP (Cisplatin for Injection) was resuspended with 10 mL WFI to produce a 1 mg/mL CDDP suspension.

For formulation 5, paclitaxel, prediluted in Cremaphor/EL and dehydrated alcohol to 6 mg/mL was further diluted to 3.3 mg/mL with WFI.

Formulation 6 was made by adding 0.9% Sodium Chloride for Injection to a vial of 10 mg of vinblastine lypholized powder.

Formulations 7–10 were prepared by diluting the appropriate amount of each test agent into saline (7—2.5 mg/mL etoposide, 8—7.5 mg/mL 5-fluorouracil, 9—3.75 mg/mL 5-fluorouracil 10—2.5 mg/mL colchicine,).

Formulation 11 was undiluted HHT-Clin, used as received.

Formulations 12 and 13 were prepared by diluting the appropriate amount of each test agent into DMSO (12—6.25 mg/mL curcumin and 13—5 mg/mL parthenolide).

Animals: Female C3H mice (Charles River Laboratories, Holister, Calif.), approximately 3 months old, were used for the study. The average body weight was approximately 25 g. Animals were maintained in isolator cages on a 12-hour light-and-dark cycle. Food and water were available ad libitum.

Tumors: The RIF-1 murine fibrosarcoma cell line was maintained in in vitro culture (Waymouth medium supplemented with 20% fetal bovine serum) at 37 C. in a humidified 5% CO2 incubator. Log-phase RIF-1 cells were trypsinized and harvested from cell culture flasks to yield a concentration of $4 \times 10^6$ cells/mL, then injected intradermally in a volume of 50 μL (equivalent to $2 \times 10^5$ cells per injection) into both flanks of each mouse. Nine days later, when tumors reached approximately 100 mm³ in size, the animals were randomized to different treatment groups.

Treatment Groups: Treatment groups are summarized in Table 4. Four to five animals were assigned to each treatment group. The intrperitoneal injection volume was 100 μL. The oral administration volume was 100 μL. Combination treatments using two test agents were administered as two separate injections, with the second one following the first either immediately or after 30 minutes.

Evaluation of Tumor Growth Delay: Tumors were measured three times weekly for up to 22 days with Vernier calipers. Tumor volume (cubic millimeters, mm³) was calculated according to the formula: $V = \pi/6 \times D1 \times D2 \times D3$ in which D1–3 are perpendicular diameters measured in millimeters (mm).

Tumor volume quadrupling time (TVQT), defined as the time required for a tumor to grow to four times (4×) its initial volume (at the time of treatment), was used as a study endpoint. The TVQT was determined for each treatment group and expressed in days as the mean±standard error (SE).

Antitumor activity or modulation of tumor growth (as measured by delayed tumor growth, i.e. increases in TVQT values) by amonafide administered as a single agent or in combination with other chemotherapeutics is presented in Table 5.

TABLE 5

Effect of Amonafide and Amonafide in Combination with Other Chemotherapeutics on RIF-1 Tumor Growth in C3H Mice

| Group | Treatment | Drug Dose (mg/Kg) | Route of Administration | Number of Tumors | TVQT |
|---|---|---|---|---|---|
| 1 | Untreated Control | — | — | 40 | 7.0 ± 0.2 |
| 2 | Amonafide-NCI/DMSO | 50 | IP | 8 | 9.7 ± 0.6 |
| 3 | Amonafide-Penta/DMSO | 50 | IP | 8 | 9.3 ± 0.3 |
| 4 | Amonafide-Penta/Saline | 30 | IP | 12 | 7.3 ± 0.2 |
| 5 | Cisplatin/WFI | 4 | IP | 16 | 9.2 ± 0.4 |
| 6 | Paclitaxel/Cremaphor EL | 10 | IP | 8 | 7.9 ± 0.3 |
| 7 | Vinblastine/Saline | 2 | IP | 8 | 8.6 ± 0.4 |
| 8 | Etoposide/Saline | 10 | IP | 8 | 8.5 ± 0.5 |
| 9 | Fluorouracil/Saline | 15 | IP | 8 | 6.7 ± 0.4 |
| 10 | Fluorouracil/Saline | 30 | IP | 8 | 13.6 ± 1.9 |
| 11 | Homoharringtonine/WFI | 4 | IP | 8 | 8.5 ± 0.5 |
| 11 | Colchicine/Saline | 10 | P0 | 8 | 6.3 ± 0.3 |
| 12 | Curcumin/DMSO | 25 | IP | 8 | 9.7 ± 1.1 |
| 13 | Parthenolide/DMSO | 20 | IP | 8 | 8.5 ± 0.8 |
| 14 | Amonafide-NCI/DMSO-30-CDDP/WFI | 50, 4 | IP, IP | 4 | 17.9 ± 0.4 |
| 15 | Amonafide-Penta/Saline-10 sec-CDDP/WFI | 30, 4 | IP, IP | 8 | 11.0 ± 0.4 |
| 16 | Amonafide-Penta/DMSO-10 sec-Paclitaxel/Cremaphor EL | 30/10 | IP, IP | 8 | 9.8 ± 0.4 |
| 17 | Amonafide-Penta/Saline-10 sec-Vinblastine/Saline | 30, 2 | IP, IP | 8 | 9.5 ± 1.1 |
| 18 | Amonafide-Penta/Saline-10 sec-Etoposide/Saline | 30, 10 | IP, IP | 8 | 8.5 ± 0.9 |
| 19 | Amonafide-Penta/Saline-10 sec-5-Fluorouracil/Saline | 30, 15 | IP, IP | 8 | 7.7 ± 0.8 |
| 20 | Amonafide-Penta/Saline-10 sec-5-Fluorouracil/Saline | 30, 30 | IP, IP | 8 | 20.2 ± 1.0 |
| 21 | Amonafide/WFI-10 sec-HHT-Clin/WFI | 30, 4 | IP, IP | 8 | 10.2 ± 0.5 |
| 22 | Amonafide-Penta/Saline-10 sec-Colchicine/WFI | 30, 10 | IP, P0 | 8 | 7.1 ± 0.3 |

TABLE 5-continued

Effect of Amonafide and Amonafide in Combination with Other
Chemotherapeutics on RIF-1 Tumor Growth in C3H Mice

| Group | Treatment | Drug Dose (mg/Kg) | Route of Administration | Number of Tumors | TVQT |
|---|---|---|---|---|---|
| 23 | Amonafide-Penta/Saline-10 sec-Curcumin | 30/25 | IP, IP | 8 | 8.2 ± 0.2 |
| 24 | Amonafide-Penta/Saline-10 sec-Parthenolide | 30/20 | IP, IP | 8 | 7.6 ± 0.3 |

Results from five separate experiments are included in this study. Untreated control animals quadrupled in size in an average of 7.0 days. Intraperitoneal administration of amonafide-NCI formulated in DMSO at 50 mg/Kg had a TVQT of 9.7 days. The additional intraperitoneal administration of CDDP further extended the mean TVQT to 17.9 days. Intraperitoneal administration of amonafide-Penta formulated in DMSO at 50 mg/Kg had a TVQT of 9.3 days. While paclitaxel (10 mg/Kg), alone, demonstrated a TVQT of 7.9 days, the addition of amonafide (50 mg/kg) extended the TVQT to 9.8 days.

Amonafide-Penta formulated in saline at 30 mg/Kg was used for the remainder of the combination studies.

At 30 mg/Kg, amonafide had an average TVQT of 7.3 days. Combination administration of cisplatin (4 mg/Kg) with amonafide (30 mg/Kg) yielded a TVQT of 11.0 days, which was greater than amonafide (TVQT=7.3 days) or cisplatin (TVQT=9.2 days), alone.

Administration of amonafide (30 mg/Kg) in combination with 5-fluorouracil (30 mg/Kg) resulted in a TVQT of 20.2 days versus 13.6 days for 5-fluorouracil, alone. At a dose of 15 mg/Kg, 5-fluorouracil gave a TVQT of 6.7 days versus 7.7 days when it was combined with amonafide at 30 mg/Kg. Combination administration of amonafide (30 mg/Kg) and vinblastine (2 mg/Kg) yielded a TVQT of 9.5 days versus 8.6 days for vinblastine, alone. Combination administration of amonafide (30 mg/Kg) and homoharringtonine (4 mg/Kg) yielded a TVQT of 10.2 days, versus 8.5 for homoharringtonie, alone. Amonafide in combination with etoposide (10 mg/Kg) gave a TVQT of 8.5 days which was the same as the TVQT for etoposide, alone. Combinations of amonafide with curcumin or parthenolide yielded TVQT's of 8.2 days and 7.6 days, respectively, which was less than curcumin (TVQT=9.7 days) or parthenolide (TVQT=8.5) as individual agents.

Orally administered colchicine (10 mg/Kg) yielded a TVQT of 6.3 days. Amonafide in combination with colchicine increased the TVQT to 7.1 days.

There were animal deaths in some groups that were recorded as follows: Two of four mice died after treatment of amonafide-NCI formulated in DMSO at 12.5 mg/mL.

In summary, intraperitoneal administration of amonafide had antitumor activity in the RIF-1 murine fibrosarcoma tumor model. Intraperitoneal administration of amonafide in combination with cisplatin, paclitaxel, vinblastine, 5-fluorouracil and homoharringtonine had antitumor activity levels greater than amonafide alone, or the individual test agents. The best combinatorial activities used cisplatin, 5-fluorouracil, and homharringtonine. Amonafide in combination with colchicine had antitumor activity less than amonafide alone. Amonafide in combination with etoposide, curcumin or parthenolide was greater than that of amonafide alone, but less than that of the test agents individually.

EXAMPLE 3

Effect of Amonafide in Combination with Camptothecin, Genistein or Rosmarinic Acid on RIF-1 Tumor Growth in C3H Mice.

Transplantable experimental murine fibrosarcomas ($2 \times 10^5$ RIF-1 cells) were grown intradermally in the flanks of 3 month old female C3H mice (Charles River, Holister, Calif.). When the tumors reached a volume of ~100 mm$^3$, the mice were randomly assigned to each experimental group (4 mice per group).

The experimental compositions were prepared as described in Table 6.

TABLE 6

| Agent | Dose | Solvent | Supplier |
|---|---|---|---|
| Amonafide | 30 mg/Kg | saline | Penta |
| Camptothecin | 6 mg/Kg | DMSO | Boehinger Ingelheim |
| Genistein | 60 mg/Kg | DMSO | ChemCon GmbH |
| Rosmarinic Acid | 20 | DMSO | Tocris |

Amonafide was manufactured by Penta for ChemGenex and was made to the appropriate concentration in saline. Genistein (ChemCon GmbH, Lot CC6700-26) Rosmarinic acid (Tocris—Batch 2/18077) and Camptotheicn (Boehinger Ingelheim- Lot 142088) were made to the appropriate concentrations in DMSO. The compositions were injected systemically (i.e., intraperitoneally, i.p.), in a volume of 100 µl. For the treatment of groups 3, 5 and 7, amonafide, was injected immediately prior to the injection of camptothecin, genistein or rosmarinic acid. After treatment, the growth of the tumors was monitored three times per week by caliper measurements of three perpendicular diameters of the tumor and calculation of tumor volume from the formula:

$$V = \pi/6 \times D_1 \times D_2 \times D_3,$$

where $D_{1-3}$ represents tumor diameters, in mm.

The data is also expressed as the tumor growth delay (TGD) median which is the median days to 4× the tumor volume from the initial treatment day, and as the delay which is the median days to 4× of the treated group minus the median days to 4× of the control group. The T/C ratio is the ratio of days to 4× of the treated tumors over the days to 4× of the untreated control tumors. Increasing values indicate increased antitumor response.

The tumors were followed until they reached 4 times their Day 0 treatment volume or up to 30 days after treatment (tumor growth delay, TGD), whichever came first. The data is also expressed as the ratio of the tumor growth delay of the treated tumor (TGD) over the untreated control group (CTGD). Increasing values of this ratio indicate increased antitumor response.

The data are presented in Table 7.

TABLE 7

| Group | Treatment | Dose (mg/kg) | TGD ± S.E. | TGD/CTGD | Median (TGD) | Delay (Days) |
|---|---|---|---|---|---|---|
| 1 | Untreated Control | — | 7.5 ± 0.6 | 0.0 | 7.3 | 0.00 |
| 2 | Amonafide | 30 | 7.0 ± 0.4 | 0.9 | 7.0 | −0.36 |
| 3 | Amonafide + Camptothecin | 30/6 | 14.9 ± 0.4 | 2.0 | 14.8 | 7.47 |
| 4 | Camptothecin | 6 | 12.9 ± 0.5 | 1.7 | 12.8 | 5.45 |
| 5 | Amonafide + Genistein | 30/60 | 8.6 ± 0.2 | 1.1 | 8.6 | 1.27 |
| 6 | Genistein | 60 | 7.9 ± 0.4 | 1.1 | 8.1 | 0.78 |
| 7 | Amonafide + Rosmarinic Acid | 30/20 | 8.9 ± 0.5 | 1.2 | 8.5 | 1.18 |
| 8 | Rosmarinic Acid | 20 | 8.4 ± 0.5 | 1.1 | 7.8 | 0.46 |

The results of Table 7 indicate that the antiproliferative activity of camptothecin, genistein and rosmarinic acid was enhanced by the use of the chemopotentiator, amonafide in that a more than additive effect was observed when both compounds were used to treat the tumor bearing mice (groups 3, 5 and 7) in comparison to the use of camptothecin, genistein or rosmarinic acid alone (groups 4, 6 and 8) or amonafide alone (group 2).

The invention claimed is:

1. A method of treatment of a host with a cellular proliferative disease, comprising contacting said host with amonafide in conjunction with an antiproliferative agent, each in an amount sufficient to have an anticancer effect on said cellular proliferative disease, wherein said cellular proliferative disease is a solid tumor, and wherein said antiproliferative agent is selected from the group consisting of vinblastine, genistein, 5-fluorouracil, paclitaxel, etoposide, curcumin, parthenolide, rosmarinic acid, and camptothecin.

2. The method according to claim 1, wherein said antiproliferative agent is camptothecin.

3. A method of treatment of a host with a cellular proliferative disease, comprising contacting said host with amonafide in conjunction with an antiproliferative agent, each in an amount sufficient to have an anticancer effect on said cellular proliferative disease, wherein said cellular proliferative disease is a solid tumor, and wherein said antiproliferative agent is selected from the group consisting of vinblastine, genistein, 5-fluorouracil, paclitaxel, etoposide, curcumin, parthenolide, and rosmarinic acid.

4. The method according to claim 1 or 3, wherein said antiproliferative agent is 5-FU.

5. The method according to claim 1 or 3, wherein said antiproliferative agent is genistein.

6. The method according to claim 1 or 3, wherein said antiproliferative agent is rosmarinic acid.

7. The method according to claim 1 or 3 wherein said host is a human.

8. The method according to claim 1 or 3 wherein said amonafide is administered before the administration of said antiproliferative agent.

9. The method according to claim 8, wherein said amonafide is administered less than 4 hours before the administration of said antiproliferative agent.

10. The method according to claim 1 or 3 wherein said amonafide is administered during the administration of said antiproliferative agent.

11. The method according to claim 1 or 3 wherein said amonafide is administered after the administration of said antiproliferative agent.

12. The method according to claim 11, wherein said amonafide is administered less than 4 hours after the administration of said antiproliferative agent.

13. The method of claim 1 or 3 wherein said anticancer effect is greater than that for said antiproliferative agent alone.

* * * * *